(12) United States Patent
Ohnishi et al.

(10) Patent No.: US 6,420,627 B1
(45) Date of Patent: Jul. 16, 2002

(54) DISPOSABLE ABSORBENT ARTICLE HAVING IMPROVED SOFT BARRIER CUFF

(75) Inventors: Kazuyuki Ohnishi, Takaishi; Ebrahim Rezai, Kobe, both of (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/554,206

(22) PCT Filed: Nov. 10, 1997

(86) PCT No.: PCT/US97/20676
§ 371 (c)(1),
(2), (4) Date: May 10, 2000

(87) PCT Pub. No.: WO99/23983
PCT Pub. Date: May 20, 1999

(51) Int. Cl.⁷ .................................................. A61F 13/15
(52) U.S. Cl. .................... 604/384; 442/60; 139/383 R; 139/420 R
(58) Field of Search ............................ 604/384; 442/60; 139/383 R, 420 R

(56) References Cited

U.S. PATENT DOCUMENTS

| | | | |
|---|---|---|---|
| 4,622,259 A | 11/1986 | McAmish et al. ........... 428/171 |
| 5,167,653 A * | 12/1992 | Igaue ..................... 604/385.02 |
| 5,531,730 A * | 7/1996 | Dreier ..................... 604/385.02 |
| 5,554,435 A * | 9/1996 | Gupta ........................ 428/224 |
| 5,714,232 A * | 2/1998 | Fenton ......................... 428/171 |

FOREIGN PATENT DOCUMENTS

| | | | |
|---|---|---|---|
| EP | 0 622 063 A2 | 11/1994 | ........... A61F/13/15 |
| EP | 0 674 035 A2 | 9/1995 | ........... D04H/1/56 |
| WO | WO 97/20532 | 6/1997 | ........... A61F/13/15 |

* cited by examiner

Primary Examiner—A. Vanatta
Assistant Examiner—Angela J Grayson
(74) Attorney, Agent, or Firm—Michael S. Kolodesh; Jay A. Krebs; Ken K. Patel

(57) ABSTRACT

The present invention is directed to a disposable absorbent article. The disposable absorbent article comprises a liquid previous topsheet; a liquid impervious backsheet combined with the topsheet; an absorbent core disposed between the topsheet and the backsheet; and a barrier cuff having a proximal edge and a distal edge, the proximal edge being joined to the topsheet and the distal edge being away from the top surface of the topsheet. The barrier cuff comprises a single layer web having a water resistance value of at least 150 mm $H_2O$, and an average bending force value of less than about 25 mg $cm^2$/cm.

15 Claims, 6 Drawing Sheets

DISPOSABLE ABSORBENT ARTICLE HAVING IMPROVED SOFT BARRIER CUFF

FIELD

The present invention relates to disposable absorbent articles. Examples of such disposable absorbent articles include disposable underwear, taped diapers, pull-on diapers, training pants, incontinence articles, catamenial devices, and disposable panties for menstrual use. The present invention more particularly relates to disposable absorbent articles having an improved soft barrier cuff.

BACKGROUND

Disposable absorbent articles such as disposable underwear, taped diapers, pull-on diapers, training pants, incontinence articles, catamenial devices, disposable panties for menstrual use and the like are well known in the art. The major function of disposable absorbent articles is to absorb and contain body exudates. Such articles are also intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article. This is most evident with loose fecal material which is not easily absorbed by the absorbent article and tends to "float" on the top surface of the absorbent article.

To improve the containment by the disposable absorbent articles, it is well known to provide barrier cuffs or flaps in the disposable absorbent articles. Examples of such barrier cuffs or flaps are disclosed in various patent publications such as U.S. Pat. No. 4,909,803 entitled "Disposable Absorbent Article Having Elasticized Flaps" issued to Aziz et al. on Mar. 20, 1990; U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989.

For many such barrier cuffs or flaps, while the soft and conformable properties of nonwoven webs used therein are expected, the barrier property thereof is also important to ensure the containment function of the disposable absorbent articles. U.S. Pat. No. 5,492,751 entitled "Disposable Garment With Improved Containment Means" issued to Buff, Sr. et al. on Feb. 20, 1996 suggests spunbond-meltblown laminated webs and spunbond-meltblown-spunbond laminated webs to improve the containment function of the barrier cuffs or flaps. However, those laminated webs may not be soft, conformable and breathable enough, thus sometimes causing skin disorders on the skin of the wearer, including diaper rash, erythema (i.e., redness), heat rash, abrasion and pressure marks. Consequently, there is still a need to improve the soft and conformable properties of the barrier cuffs while ensuring the containment function of the disposable absorbent articles.

SUMMARY

The present invention is directed to a disposable absorbent article. The disposable absorbent article comprises a liquid previous topsheet; a liquid impervious backsheet combined with the topsheet; an absorbent core disposed between the topsheet and the backsheet; and a barrier cuff having a proximal edge and a distal edge, the proximal edge being joined to the topsheet and the distal edge being away from the top surface of the topsheet. The barrier cuff comprises a single layer web having a water resistance value of at least about 150 mmH$_2$O, and an average bending force value of less than about 25 mg cm$^2$/cm.

These and other features, aspects, and advantages of the present invention will become evident to those skilled in the art from a reading of the present disclosure.

BRIEF DESCRIPTION OF THE DRAWINGS

While the specification concludes with claims particularly pointing out and distinctly claiming the invention, it is believed that the invention will be better understood from the following description of preferred embodiments which is taken in conjunction with the accompanying drawings and which like designations are used to designate substantially identical elements, and in which:

DETAILED DESCRIPTION

Figure 1:
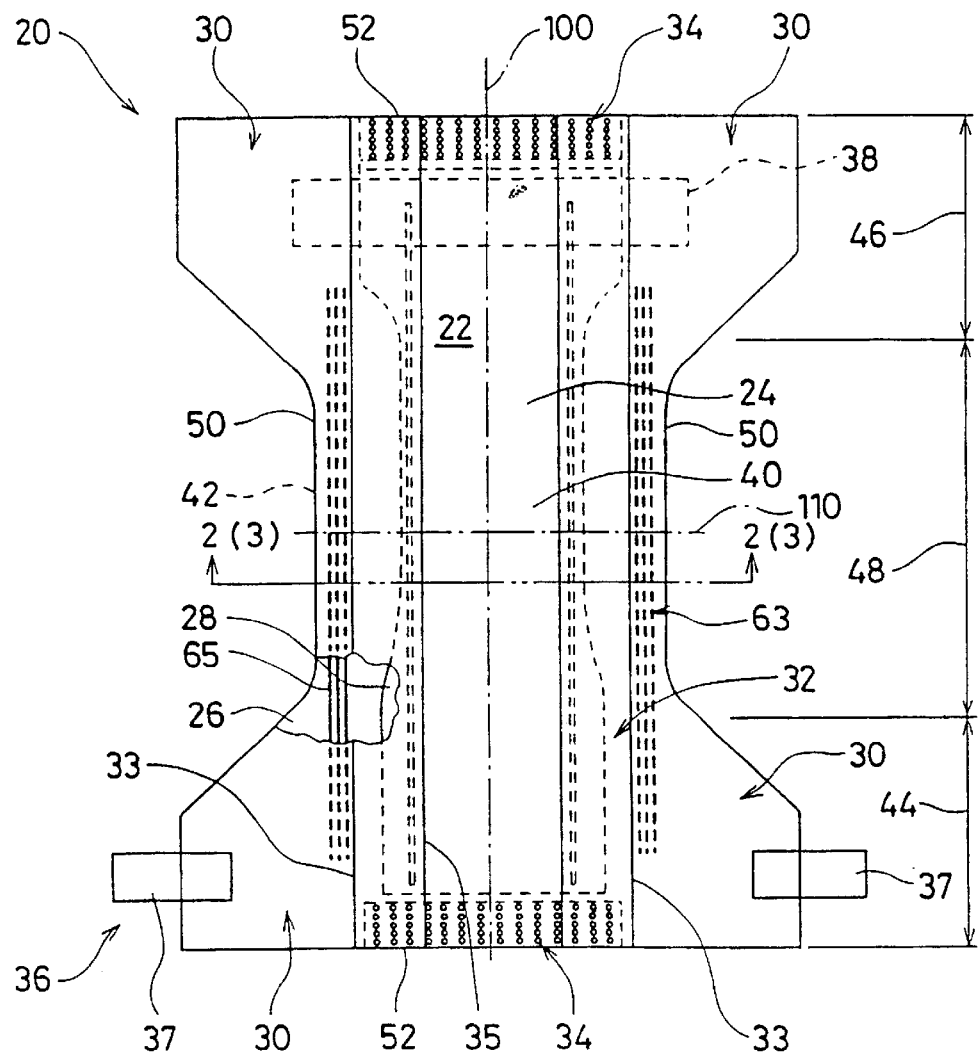
FIG. 1 is a plan view of a preferred embodiment of the disposable absorbent article of the present invention having portions cut away to reveal underlying structure, with the inner surface of the article facing the viewer.

All cited references are incorporated herein by reference in their entireties. Citation of any reference is not an admission regarding any determination as to its availability as prior art to the claimed invention.

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A preferred embodiment of an absorbent article of the present invention is the disposable absorbent article, diaper 20, shown in FIG. 1. As used herein, the term "diaper" refers to an absorbent article generally worn by infants and incontinent persons that is worn about the lower torso of the wearer. It should be understood, however, that the present invention is also applicable to other absorbent articles such as pull-on garments, incontinence briefs, incontinence undergarments, diaper holders and liners, feminine hygiene garments, training pants, and the like. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element.

As is already stated, it is well known to provide barrier cuffs or flaps in the disposable absorbent articles to improve the containment by the disposable absorbent articles.

I. Barrier Cuff

The barrier cuff of the present invention has a proximal edge and a distal edge. The proximal edge is joined to the topsheet of the absorbent article while the distal edge is away from the top surface of the topsheet. The distal edge is not secured to any other portion of the absorbent article so that it may be spaced away from the top surface of the topsheet. The distal edge is preferably spaced away from the top surface of the topsheet so that the barrier cuff may form a channel to enhance the containment characteristics of the article. As used herein, "spaced" includes embodiments wherein the distal edge may assume one or more positions relative to the top surface of the topsheet including at some times assuming a position adjacent the top surface of the topsheet. The distance between the distal edge to the top surface of the topsheet is measured along a line drawn from the distal edge to the closest part of the topsheet when the distal edge is positioned so as to be spaced away from the topsheet as far as possible. (i.e., in the elastically contracted position). Preferably, the distal edge is spaced away from the topsheet by a height of at least about 2 mm, and more preferably of from about 5 mm to about 60 mm.

The channel is formed at least along the proximal and distal edges and the inboard surface of the barrier cuff. The channel forms a barrier to the flow of exudates as they tend to move or float across the topsheet. Thus the channel holds and contains exudates until the diaper can be removed.

Preferably, the disposable absorbent article further comprises a spacing means combined with the barrier cuff for spacing the distal edge away from the top surface of the topsheet. The spacing means can be any member which gathers, contracts, stiffens, shortens or otherwise acts on the barrier cuff so as to cause a channel to be formed along the barrier cuff to provide a constraint against the leakage of exudates.

Preferably, the spacing means comprises a spacing elastic member secured adjacent the distal edge inside of the barrier cuff. The spacing elastic member is preferably secured to the barrier cuff in an elastically contractible condition so that in a normally unrestrained configuration, the spacing elastic member effectively contracts or gathers the barrier cuff.

In preferred embodiments, the barrier cuff of the present invention is a barrier leg cuff or a barrier waist cuff, or the both. As used herein, the term "barrier leg cuff" is used to describe the barrier cuff is provided almost parallel to the side edge of the absorbent article. Preferably, the barrier leg cuff is provided inboard of and more preferably adjacent to the gasketting cuff which is provided along the side edge of the absorbent article. As used herein, the term "barrier waist cuff" is used to describe the barrier cuff is provided almost parallel to the end edge of the absorbent article. Preferably, the barrier waist cuff is provided inboard of and more preferably adjacent to the waistband which is provided along the end edge of the absorbent article.

Figure 2:
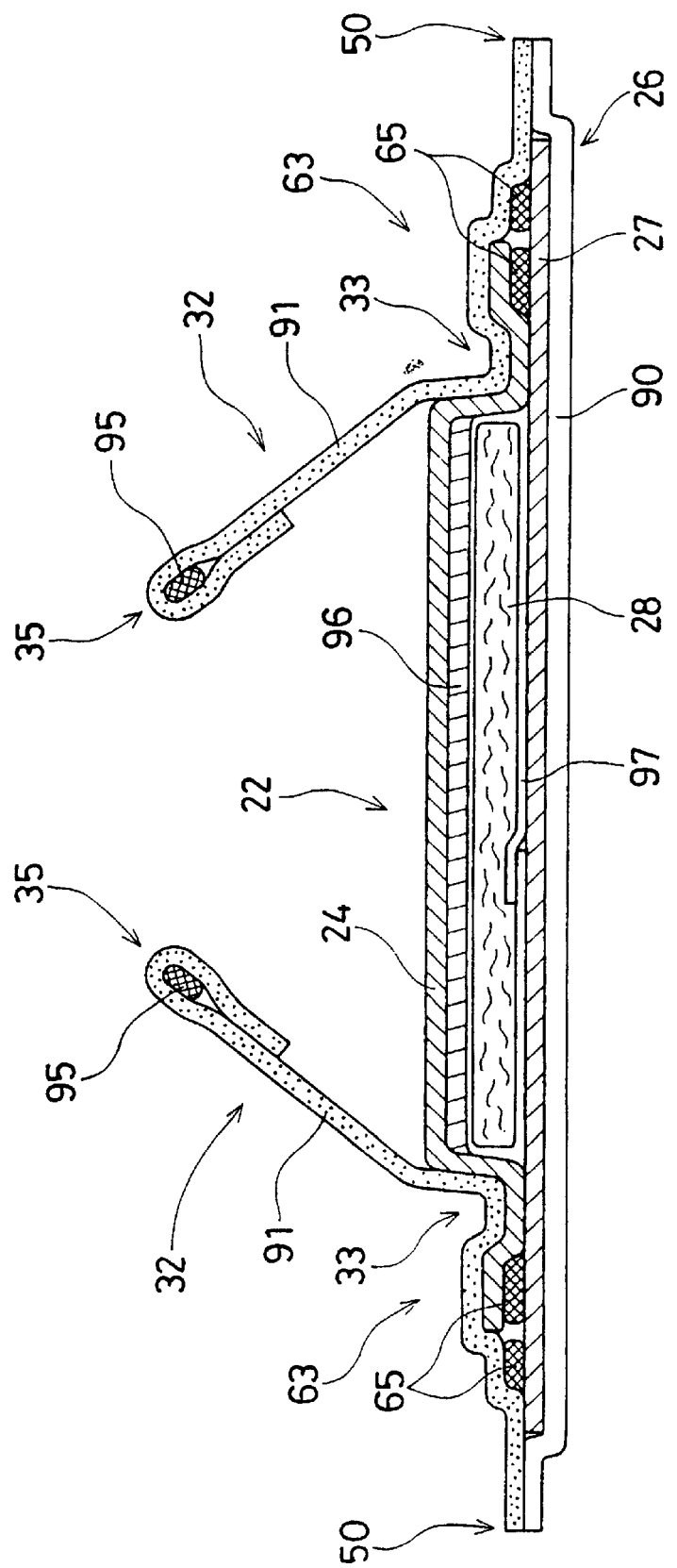
FIG. 2 is a cross-sectional view of a preferred embodiment taken along the section line 2—2 of FIG. 1.
Figure 3:
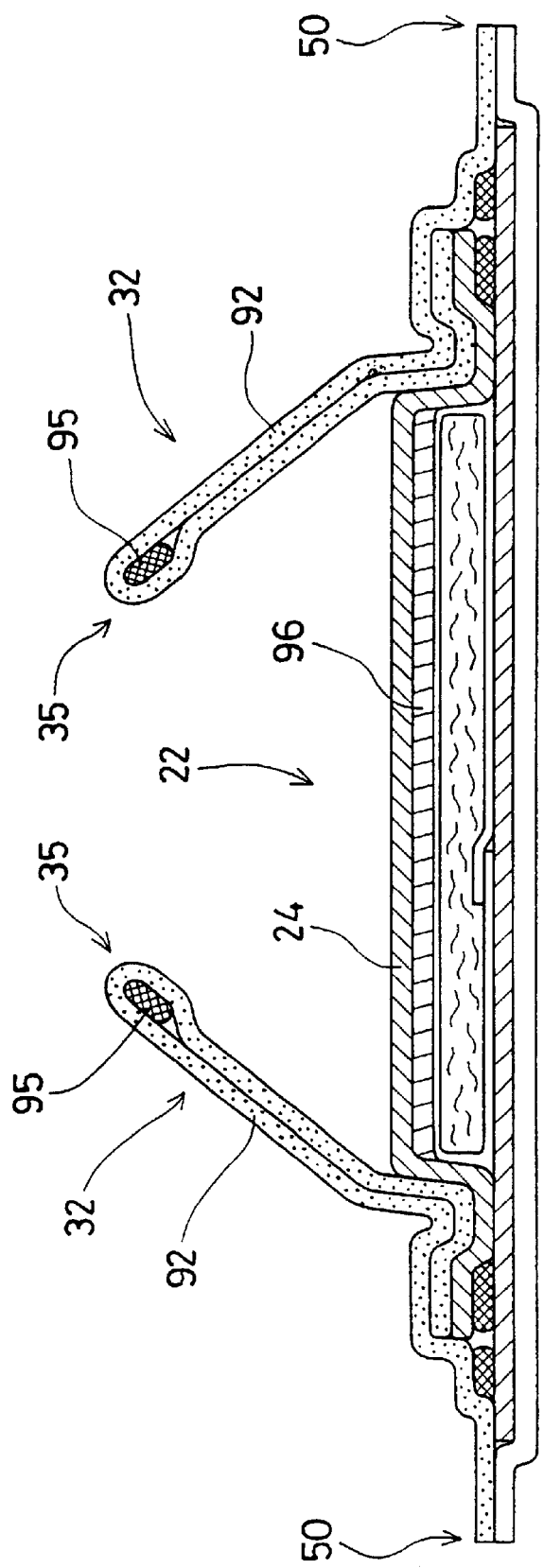
FIG. 3 is a cross-sectional view of another preferred embodiment taken along the section line 3—3 of FIG. 1.
Figure 5:
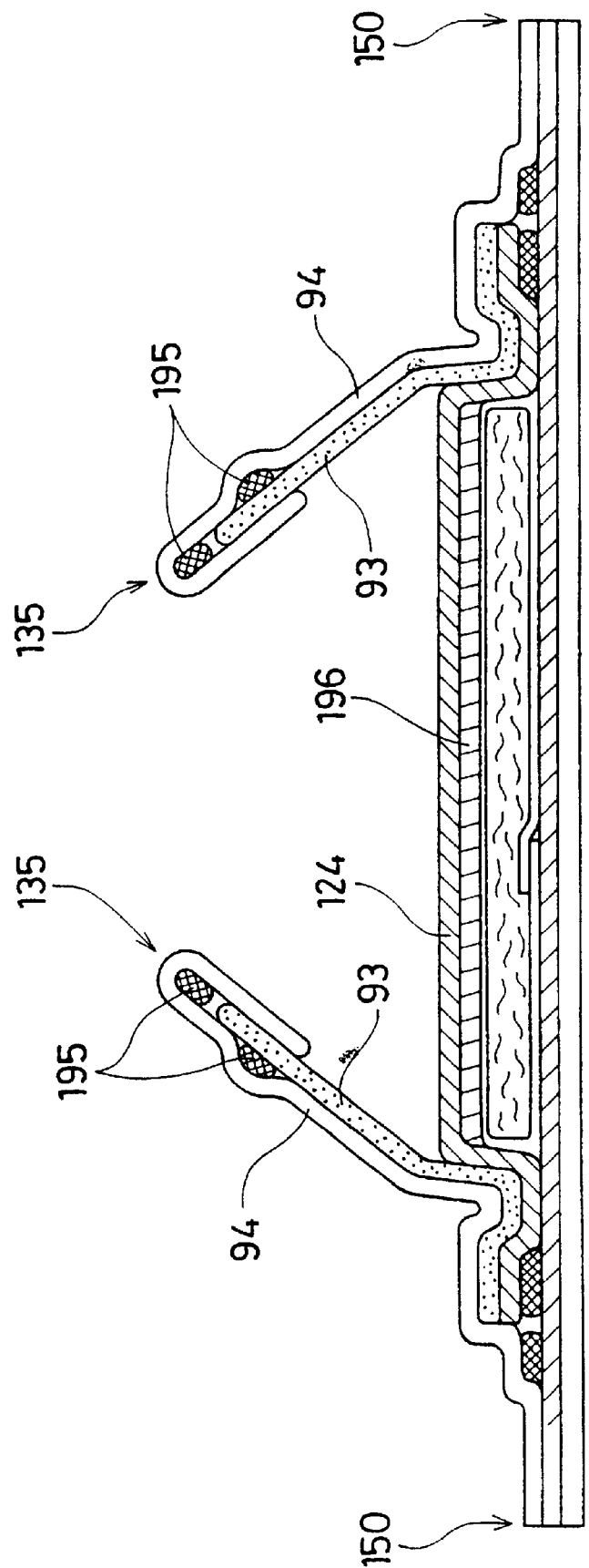
FIG. 5 is a cross-sectional view taken along the section line 5—5 of FIG. 4.

The barrier cuff of the present invention comprises a single layer web. As used herein, the term "single layer" is used herein to describe that the web has a first surface and a second surface opposed to the first surface, wherein at least corresponding portions of the first and second surfaces are not joined to any other material before it is joined to the absorbent articles of the present invention. In another preferred embodiment, the barrier cuff further comprises another web which is joined to the single layer web to form the barrier cuff (an example is shown in FIG. 5). In an yet alternative preferred embodiment, the barrier cuff comprises a two layered structure of the single layer web. As used herein, the term "two layered structure" is used herein to describe the structure where at least a part of two single layer webs are joined. Preferably, the two layered structure is formed by folding at least a part of the single layer web (examples are shown in FIGS. 2 and 3).

The single layer web of the present invention has a water resistance value of at least about 150 mmH$_2$O. Preferably, the single layer web has a water resistance value of at least about 20 mmH$_2$O, more preferably of at least about 300 mmH$_2$O. The water resistance value is determined by the "Water static pressure method" described in the section entitled "Testing Methods for Water Resistance of Textiles" of Japanese Industrial Standard No. L 1092. The water resistance value is obtained as an average value of the hydrostatic head value (mmH$_2$O) measured in accordance with the above method.

The single layer web of the present invention has an average bending force value of less than about 25 mg cm$^2$/cm. Preferably, the single layer web has an average bending force value of less than about 20 mg cm$^2$/cm, more preferably of less than about 15 mg cm$^2$/cm. The average bending force value is determined by the following measurements and calculation.

Bending Force Value Measurement and Calculation

Figure 6A:
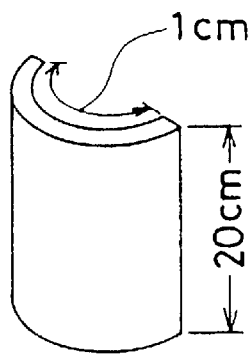
FIGS. 6A and 6B are schematic diagrams illustrating a specimen used for measuring bending force value.
Figure 6B:
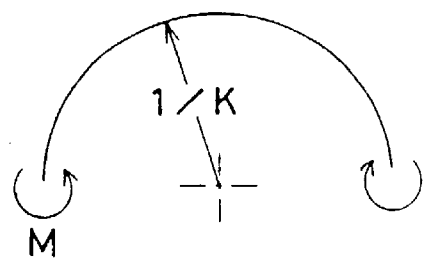
Figure 7:
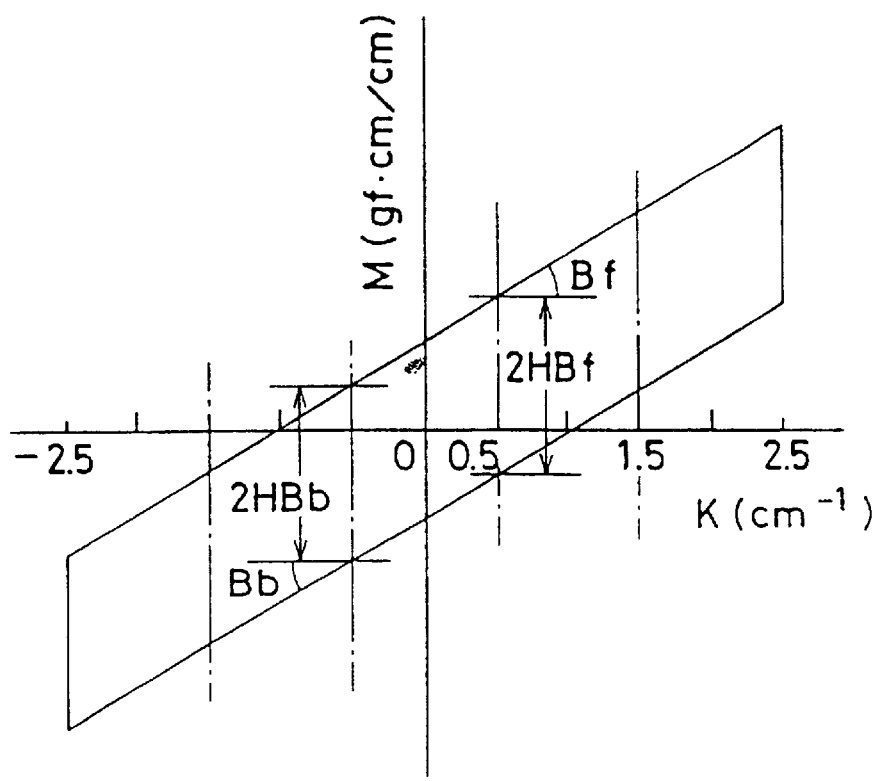
FIG. 7 is a graph showing the bending hysteresis curve of a measured specimen.

The bending, force value is a measure of the force required to bend a specimen. The deformation mode is a pure bending between the curvature K=−2.5 cm$^{-1}$ and 2.5 cm$^{-1}$. The effective dimension for the measurement is 20 cm in length and 1.0 cm in width (rectangular). The specimen is bent as shown in FIGS. 6A and 6B. The bending rate is 0.5 cm$^{-1}$/sec. As a result, the bending hys-ter-e-sis curve as shown in FIG. 7 is obtained by the measurement. The horizontal axis shows the curvatures K cm$^{-1}$ and the vertical axis shows the moment M (gf·cm/cm). The bending force value of B is calculated as follows:

$$B=(Bf+Bb)/2 \qquad (1)$$

where Bf and Bb are the slopes of the hysteresis curves between K =0.5 cm$^{-1}$ and 1.5 cm$^{-1}$ and K=0.5 cm$^{-1}$ and −1.5 cm$^{-1}$ respectively.

Measurements are carried out in the MD and CD directions of the same web specimen. The average bending force value is the mean value of the above B values obtained from the measurements about the MD and CD directions of the specimen.

In a preferred embodiment, the barrier cuff comprises a two layered structure of the single layer web having a water resistance value of at least about 150 mmH$_2$O, an average bending force value of less than about 21 mg cm$^2$/cm. Preferably, the single layer web has a water resistance value of at least about 200 mmH$_2$O, and an average bending force value of less than about 13 mg cm$^2$/cm.

Preferably, the single layer web of the present invention has a basis weight of from about 3 g/m$^2$ to about 30 g/m$^2$. More preferably, the single layer web has a weight of from about 7 g/m$^2$ to about 20 g/m$^2$, yet more preferably from about 10 g/m$^2$ to about 15 g/m$^2$.

In a preferred embodiment, the single layer web of the present invention has an air permeability value of at least about 10 cm$^3$/cm$^2$/sec. More preferably, the single layer web has an air permeability value of at least 20 cm$^3$/cm$^2$/sec, more preferably of at least 30 cm$^3$/cm$^2$/sec. The air permeability value is determined by using a Frazir type tester described in Section 6.27, entitled "Air Permeability" of Japanese Industrial Standard No. L 1096. The air permeability value is obtained as the air volume which is passed through the specimen (cm$^3$/cm$^2$ sec), measured in accordance with the above method.

Preferably, the single layer web of the present web has a maximum tensile strength value of at least about 0.7 kgf. More preferably, the single layer web has a maximum tensile strength value of at least 1.0 kgf, more preferably of at least 1.3 kgf. The maximum tensile strength value is measured and determined according to Section 5.4, entitled "Tensile Strength and Extension Ratio" of Japanese Industrial Standard No. L 1085. The specimen has 30 cm of length and 5 cm width. The specimen holding distance to be measured (i.e., the distance between two holding grips) is 20 cm. The tensile rate is 20 cm/min. The maximum tensile strength value is obtained as the maximum value of the tensile strength (kgf) before the specimen is broken completely.

The single layer web is compliant, soft feeling, and non-irritating to the wearers skin. In a preferred embodiment, the single layer web is a meltblown nonwoven web made of synthetic fibers, for example, polymeric fibers such as polyester, polyolefin (i.e., polypropylene (PP), polyethylene (PE), propylen random copolymer, etc.) and styrenic thermoplastic elastomer fibers, and mixture fibers thereof. Preferably, the meltblown nonwoven web is made of fine fibers of a polypropylene (PP). The meltblown nonwoven web can be made by any conventional manufacture process which is known by those of ordinary skill in the art as long the single layer web has the above described range of values (i.e., the water resistance value and the bending force value). Preferred processes for making meltblown nonwoven webs are disclosed in U.S. Pat. No. 3,978,185 to Buntin et al. on Aug. 31, 1976, and U.S. Pat. No. 4,622,259 to McAmish et al. on Nov. 11, 1986.

In a more preferred embodiment, the single layer web is formed by an elongation along its machine direction while or after the web is produced from its manufacture line and before it is joined to the absorbent articles, thereby to make the single layer web softer. A preferred elongation rate is from about 5% to about 150%, more preferably of from 60% to 80%. In preferred embodiments, the single layer web is a meltblown nonwoven web made of synthetic fibers. Preferably, the meltblown nonwoven web is made of fine fibers of a polypropylene (PP).

In a more preferred embodiment, the single layer web has an embossment pattern. As used herein, the term "embossment" is used herein to describe the web has at least a portion where the web was pressed and heated before it is used in the disposable absorbent article of the present invention. As used herein, the term "pattern" is used herein to describe the embossed portion(s) of the web has a predetermined arrangement. In preferred embodiments, the predetermined arrangement comprises a plurality of discrete embossed portions. The embossment pattern can be any pattern known by those skilled in the art such as spots, lattice, diagonal, interrupted-line and the like. Preferably, the embossment pattern is formed by passing the web between a pair of heated bonding rolls (i.e., embossment rolls) which have a corresponding pattern to a desired embossment pattern. The web is compressed and heated by the bonding rolls in accordance with the pattern on the rolls to create the embossment pattern in which the particular filaments and/or fibers are bonded. The embossment pattern can increase the strength of the web against the friction which is applied by the skin of wearer when the article is used. The improvement of increase in the strength of the web against the friction can be confirmed by Martindale Friction Test.

The embossment ratio of the single layer web is defined by the ratio of the total area of embossing portion to the total area of non-embossing portion of the heated bonding rolls. Preferably, the embossment ratio of the single layer web is at least 0.5%, more preferably from about 1% to about 35%.

II. Absorbent Article

FIG. 1 is a plan view of the diaper 20 in its flat-out, uncontracted state (i.e., with elastic induced contraction pulled out) with portions of the structure being cut-away to more clearly show the construction of the diaper 20 and with the portion of the diaper 20 which faces the wearer, i.e., the inner surface 40, facing the viewer. As shown in FIG. 1, the diaper 20 preferably comprises a containment assembly 22 comprising a liquid previous topsheet 24; a liquid impervious backsheet 26 joined to the topsheet; and an absorbent core 28 positioned between the topsheet 24 and the backsheet 26. The diaper preferably further comprises side panels 30; elasticized leg cuffs 32; elasticized waistbands 34; and a fastening system 36 preferably comprising a pair of securement members 37 and a landing member 38. The backsheet 26 prevents the exudates absorbed and contained in the absorbent core 28 from wetting articles which contact the diaper 20 such as bed sheets and undergarments.

The diaper 20 has an inner surface 40 (facing the viewer in FIG. 1), an. outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the side edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearer's body (i.e., the outer surface 42 is generally formed by at least a portion of the backsheet 26 and other components joined to the backsheet 26). The rear waist region 44 and the front waist region 46 extend from the end edges 52 of the periphery to the crotch region 48.

The diaper 20 also has two centerlines, a longitudinal centerline 100 and a transverse centerline 110. The term "longitudinal", as used herein, refers to a line, axis, or direction in the plane of the diaper 20 that is generally aligned with (e.g. approximately parallel with) a vertical plane which bisects a standing wearer into left and right halves when the diaper 20 is worn. The term "transverse", as used herein, refers to a line, axis or direction which lies within the plane of the diaper that is generally perpendicular to the longitudinal direction (which divides the wearer into front and back body halves).

The topsheet 24 and the backsheet 26 have length and width dimensions generally larger than those of the absorbent core 28. The topsheet 24 and the backsheet 26 extend beyond the edges of the absorbent core 28 toward the periphery of the diaper 20. While the topsheet 24, the backsheet 26, and the absorbent core 28 may be assembled in a variety of well known configurations, exemplary containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

The absorbent core 28 may be any absorbent member which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

As shown in FIG. 1, a preferred embodiment of the diaper 20 has an asymmetric, modified T-shaped absorbent core 28 having ears in the front waist region but a generally rectangular shape in the rear waist region. Other exemplary absorbent structures for use as the absorbent core 28 that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany eit al., on Aug. 10,1993; and in U.S. Pat. No. 5,147,345, entitled "High Efficiency Absorbent Articles For Incontinence Management" issued to Young, LaVon and Taylor on Sep. 15, 1992.

The topsheet 24 is preferably positioned adjacent the inner surface of the absorbent core 28 and is preferably joined thereto and to the backsheet 26 by attachment means (not shown) such as those well known in the art. The backsheet 26 may be joined to the absorbent core 28 in any suitable manner known by those of skill in the art. In a preferred embodiment, the topsheet 24 and the backsheet 26 are joined directly to each other in the diaper periphery and are indirectly joined together by directly joining them to the absorbent core 28 by any suitable attachment means.

The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. The topsheet 24 is preferably made of a hydrophobic material to isolate the wearer's skin from liquids which have passed through the topsheet 24 and are contained in the absorbent core 28 (i.e., to prevent rewet). If the topsheet 24 is made of a hydrophobic material, at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. Nos. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991.

In preferred embodiments, the topsheet 24 is a nonwoven web that can provide reduced tendency for surface wetness; and consequently facilitate maintaining urine absorbed by the core 28 away from the user's skin, after wetting.

One of the preferred topsheet materials is a conventional thermobonded carded web which is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. The first topsheet layer is preferably a polypropylene/polypropylene bicomponent fiber, e.g., a lower melting temperature polypropylene in sheath and a higher melting temperature polypropylene in the core of the fiber. The second topsheet layer is preferably a polyethylene/polyethylene telephthalate bicomponent fiber, e.g., a lower melting temperature polyethylene in the sheath and a higher melting temperature and more resilient polyethylene telephthalate in the core of the fiber. The first topsheet layer preferably has a weak hydrophilic surfactant and the second topsheet layer preferably has a normal hydrophilic surfactant. The total basis weight of a typical material is about 20 to 22 g/m$^2$.

Referring to FIG. 2, in a preferred embodiment of the diaper 20, the containment assembly 22 further comprises an acquisition/distribution layer 96 between the topsheet 24 and absorbent core 28. The acquisition/distribution layer 96 is provided to help reduce the tendency for surface wetness of the topsheet 24. The acquisition/distribution layer 96 preferably comprises carded, resin bonded hiloft nonwoven materials such as, for example, available as Code No. FT-6860 from Polymer Group, Inc., North America (Landisiville, N.J., U.S.A.), which is made of polyethylene telephthalate fibers of 6 dtex, and has a basis weight of about 43 g/m². In another preferred embodiment, the acquisition/ distribution layer 96 may comprise chemically treated stiffened cellulosic fiber material, available from Weyerhaeuser Co. (United States) under the trade designation of CMC. In still another preferred embodiment, the acquisition/ distribution layer 96 comprises conventional cellulosic fluff material, also known as wood pulp fiber, available from Weyerhaeuser Co. (United States) under the trade name FLINT RIVER.

Another preferred topsheet 24 comprises an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel. et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr et al. on Jul. 31, 1984; and U.S. Pat. No. 5,006,394 "Multilayer Polymeric Film" issued to Baird on Apr. 9, 1991.

Again referring to FIG. 2, the backsheet 26 comprises a nonwoven web 90 positioned at the outermost portion of the diaper 20, which covers at least a portion of the outermost portion of the absorbent article. In preferred embodiments, the nonwoven web 90 covers at least 30%, more preferably at least 70%, most preferably at least 90%, of the area of the outermost portion of the diaper 20. In preferred embodiments, the backsheet 26 further comprises a plastic film 27 having an outer-facing surface and a body-facing surface, and the nonwoven web 90 is joined with the outer-facing surface of the plastic film 27 to form a laminate (i.e., the backsheet 26). The nonwoven web 90 may be joined to the plastic film 27 by any suitable attachment means known in the art. For example, the nonwoven web 90 may be secured to the plastic film 27 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2476-01, and a hotmelt adhesive obtainable from H.B. Fuller Japan Co., Ltd., Osaka, Japan as JM-6064. Preferably, the density of the adhesive applied between the nonwoven web 90 and the plastic film 27 is from about 0.05 g/m² to about 7.0 g/m², more preferably from about 0.1 g/m² to about 5.0 g/m², most preferably from about 0.2 g/m² to about 1.5 g/m².

The plastic film 27 is preferably impervious to liquids (e.g., urine) and is preferably manufactured from a thin plastic film. However, preferably the plastic film permits vapors to escape from the diaper 20. In a preferred embodiment, a microporous polyethylene film is used for the plastic film 27. A suitable microporous polyethylene film is manufactured by Mitsui Toatsu Chemicals, Inc., Nagoya, Japan and marketed in the trade as ESPOIR No.

A suitable material for the plastic film 27 is a thermoplastic film having a thickness of from about 0.012 mm (0.5 mil) to about 0.051 mm (2.0 mils), preferably comprising polyethylene or polypropylene. Preferably, the plastic film has a basis weight of from about 5 g/m² to about 35 g/m². However, it should be noted that other flexible liquid impervious materials may be used. As used herein, the term "flexible" refers to materials which are compliant and which will readily conform to the general shape and contours of the wearer's body.

In a preferred embodiment, the plastic film 27 exists only in the containment assembly area 22 (and does not exist the side panel areas 30), while the nonwoven web 90 exists the both of the containment assembly area 22 and the side panel areas 30. In this embodiment, the nonwoven web 90 covers all of the outer-facing surface 70 of the plastic film 27.

In a preferred embodiment, the nonwoven web 90 is a carded nonwoven web, for example, obtainable from Havix Co., LTD., Gifu, Japan as E-2341. The nonwoven web is made of bi-component fibers of a polyethylene (PE) and a polyethylene terephthalate (PET). The ratio of PE/PET is about 40/60. The PE/PET bi-component fiber has the dimension of 2d×51 mm.

In another preferred embodiment, the nonwoven web 90 is a spunbonded nonwoven web, for example, obtainable from Mitsui Petrochemical Industries, Ltd., Tokyo, Japan. The nonwoven web is made of bi-component fibers of a polyethylene (PE) and a polypropylene (PP). The ratio of PE/PP is about 80/20. The PE/PP bi-component fiber has the thickness is approximately 2.3d.

The backsheet 26 is preferably positioned adjacent the outer surface of the absorbent core 28 and is preferably joined thereto by any suitable attachment means known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment means may comprise heat bonds, pressure bonds, ultrasonic bonds, dynamic mechanical bonds, or any other suitable attachment means or combinations of these attachment means as are known in the art.

In a preferred embodiment, the absorbent core 28 is not joined to the backsheet 26, and/or the topsheet 24 in order to provide greater extensibility in the front waist region 46 and the rear waist region 44. Alternative embodiments are contemplated wherein an additional member, such as a liquid impervious barrier material(s) (not shown), is positioned between the outer surface of the absorbent core 28 and the backsheet 28. Any such barrier member may or may not be joined to the absorbent core 28. Further, the backsheet 26 may or may not be joined to any barrier material(s) that are positioned between the backsheet 26 and the absorbent core 28.

It may also be desirable to provide the diaper with extensibility or elasticity in all or a portion of the side panels 30. (As used herein, the term "extensible" refers to materials that are capable of extending in at least one direction to a certain degree without undue rupture. The terms "elasticity" and "elastically extensible" refer to extensible materials that have the ability to return to approximately their original dimensions after the force that extended the material is removed. As used herein, any material or element described as "extensible" may also be elastically extensible unless otherwise provided.) Extensible side panels 30 provide a more comfortable and contouring fit by initially conformably fitting the diaper to the wearer and sustaining this fit throughout the time of wear well passed when the diaper has been loaded with exudates since the side panels allow the sides of the diaper to expand and contract. Extensible side panels 30 further provide more effective application of the diaper 20 since even if the diaperer pulls one side panel 30 farther than the other during the application (asymmetrically), the diaper 20 will "self-adjust" during wear. While the extensible side panels 30 may be constructed in a number of configurations, examples of diapers with extensible side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983;, U.S. Pat. No. 4,938,753 issued to Van Gompel, et al. on Jul. 3, 1990; and in U.S. Pat. No. 5,151,092 issued to Buell et al. on Sep. 29, 1992.

The extensible side panels 30, or any other elements of the diaper 20 in which extensibility or elasticity is desirable such as the waistbands 34, may comprise materials that have been "prestrained", or "mechanically prestrained" (i.e., subjected to some degree of localized pattern mechanical stretching to permanently elongate the material), or structure elastic-like webs (SELF), as described below. The materials may be prestrained using deep embossing techniques as are known in the art. Alternatively, the materials may be prestrained by directing the material through an incremental mechanical stretching system as described in U.S. Pat. No. 5,330,458 entitled "Absorbent Article With Elastic Feature Having A Portion Mechanically Prestrained" issued to Buell et al., on Jul. 19, 1994. The materials are then allowed to return to their substantially untensioned condition, thus forming a zero strain stretch material that is extensible, at least up to the point of initial stretching. Examples of zero strain materials are disclosed in U.S. Pat. No. 2,075,189 issued to Galligan on Mar. 30, 1937; U.S. Pat. No. 3,025,199 issued to Harwood on Mar. 13, 1962; U.S. Pat. Nos. 4,107, 364 and 4,209,563 issued to Sisson on Aug. 15, 1978 and Jun. 24, 1980, respectively; U.S. Pat. No. 4,834,741 issued to Sabee on May 30, 1989; and U.S. Pat. No. 5,151,092 issued to Buell et al., on Sep. 29, 1992.

Alternatively, the extensible side panels 30 or any portions of the side panels 30 or the materials included in the side panels or any other element of the diaper 20 in which extensibility is desirable may comprise a structural elastic-like film (SELF) web. A structural elastic-like film web is an extensible material that exhibits an elastic-like behavior in the direction of elongation without the use of added elastic materials. The SELF web includes a strainable network having at least two contiguous, distinct, and dissimilar regions. One of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages on controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable and the method for making such webs are more completely described in the co-pending, commonly assigned U.S. patent application Ser. No. 08/203,456, which has been allowed, entitled "Absorbent Article With Multiple Zone Structural Elastic-Like Film Web Extensible Waist Feature" filed by Donald C. Roe, et al. on Feb. 24, 1994; and in the co-pending, commonly assigned U.S. patent application Ser. No. 08/203,087 entitled "Web Materials Exhibiting Elastic-Like Behavior" filed by Charles W. Chappell, et al. on Feb. 28, 1994.

The diaper 20 preferably further comprises an elasticized waistband 34 that provides improved fit and containment. The elasticized waistband 34 is that portion or zone of the diaper 20 which is intended to elastically expand and contract to dynamically fit the wearer's waist. The elasticized waistband 34 preferably extends longitudinally outwardly from at least one of the waist edges of the absorbent core 28 and generally forms at least a portion of the end edge of the diaper 20. Disposable diapers are generally constructed so as to have two elasticized waistbands, one positioned in the rear waist region and one positioned in the front waist region, although diapers can be constructed with a single elasticized waistband. Further, while the elasticized waistband 34 or any of its constituent elements can comprise a separate element affixed to the diaper 20, the elasticized waistband 34 may be constructed as an extension of other elements of the diaper such as the backsheet 26 or the topsheet 24, preferably both the backsheet 26 and the topsheet 24. Embodiments are also contemplated wherein the elasticized waistband 34 comprises apertures, as described above, to provide breathability in the waist regions. The elasticized waistband 34 may be constructed in a number of different configurations including those described in U.S. Pat. No. 4,515,595 entitled "Disposable Diapers with Elastically Contractible Waistbands" issued to Kievit et al. on May 7, 1985 and the above referenced U.S. Pat. No. 5,151,092 issued to Buell.

The diaper 20 further comprises elasticized barrier leg cuffs 32 for providing improved containment of liquids and other body exudates. The barrier leg cuffs 32 may be comprised of several different embodiments for reducing the leakage of body exudates in the leg regions. Exemplary embodiments are disclosed in the following U.S. patents. U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S.

Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

FIG. 2 is a cross-sectional view of the diaper shown in FIG. 1 taken along the section line 2—2. Referring to FIG. 2, the elasticized leg cuff 32 has a proximal edge 33 and a distal edge 35. The distal edge 35 of the elasticized leg cuff 32 is that part of the elasticized leg cuff 32 which is spaced away from the containment assembly 22 of the diaper when the diaper 20 is being worn. The proximal edge 33 is that part of the elasticized leg cuff 32 which is joined to the containment assembly 22 of the diaper 20. The proximal edge 33 is generally located laterally inboard of the periphery of the diaper 20. A portion of the elasticized leg cuff 32, however, may extend laterally outwardly from the proximal edge 33 such that the material covers at least a portion of the outer region of the backsheet 26 (not shown). An example of an elasticized cuff 32 having a portion extending laterally outwardly over most or all of the outer region of the backsheet 26 is described in the above-referenced U.S. Pat. No. 4,795,454 issued to Dragoo.

The elasticized barrier leg cuff 32 shown in FIG. 2 is formed by a single layer web of meltblown nonwoven web 91. The meltblown nonwoven web 91 is folded at the distal edge 35 to enclose the spacing elastic member 95. The meltblown nonwoven web 91 extends to the side edge 50 of the diaper 20. Preferably, the meltblown nonwoven web 91 has a water resistance value of at least about 200 mmH$_2$O, and an average bending force value of less than about 20 mg cm$^2$/cm. More preferably, the meltblown nonwoven web 91 has a water resistance value of at least about 300 mmH$_2$O, and an average bending force value of less than about 15 mg cm$^2$/cm.

The containment assembly 22 comprises the acquisition/distribution layer 96 between the topsheet 24 and absorbent core 28. The absorbent core 28 may be wrapped by a tissue web 97.

Another preferred embodiment of the elasticized barrier leg cuff 32 is shown in FIG. 3. The elasticized barrier leg cuff 32 of FIG. 3 comprises, a two layered structure formed by a single layer web of meltblown nonwoven web 92. The meltblown nonwoven web 92 it folded at the distal edge 35 to enclose the spacing elastic member 95 and to form the two layered structure. The meltblown nonwoven web 92 extends to the side edge 50 of the diaper 20. Preferably, the meltblown nonwoven web 92 has a water resistance value of at least about 200 mmH$_2$O, and an average bending force value of less than about 13 mg cm$^2$/cm.

Referring to FIG. 1, the diaper 20 also comprises a fastening system 36 which forms a side closure which maintains the rear waist region 44 and the front waist region 46 in an overlapping configuration such that lateral tensions are maintained around the circumference of the diaper to maintain the diaper on the wearer. Exemplary fastening systems are disclosed in U.S. Pat. No. 3,848,594 issued to Buell on Nov. 19, 1974; U.S. Pat. No. 4,662,875 issued to Hirotsu and Robertson on May 5, 1987; U.S. Pat. No. 4,869,724 issued to Scripps on Sep. 26, 1989; U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; and U.S. Pat. No. 5,326,612 entitled "Nonwoven Female Component For Refastenable Fastening Device And Method of Making the Same" issued to David J. K. Goulait on Jul. 5, 1994.

Figure 4:
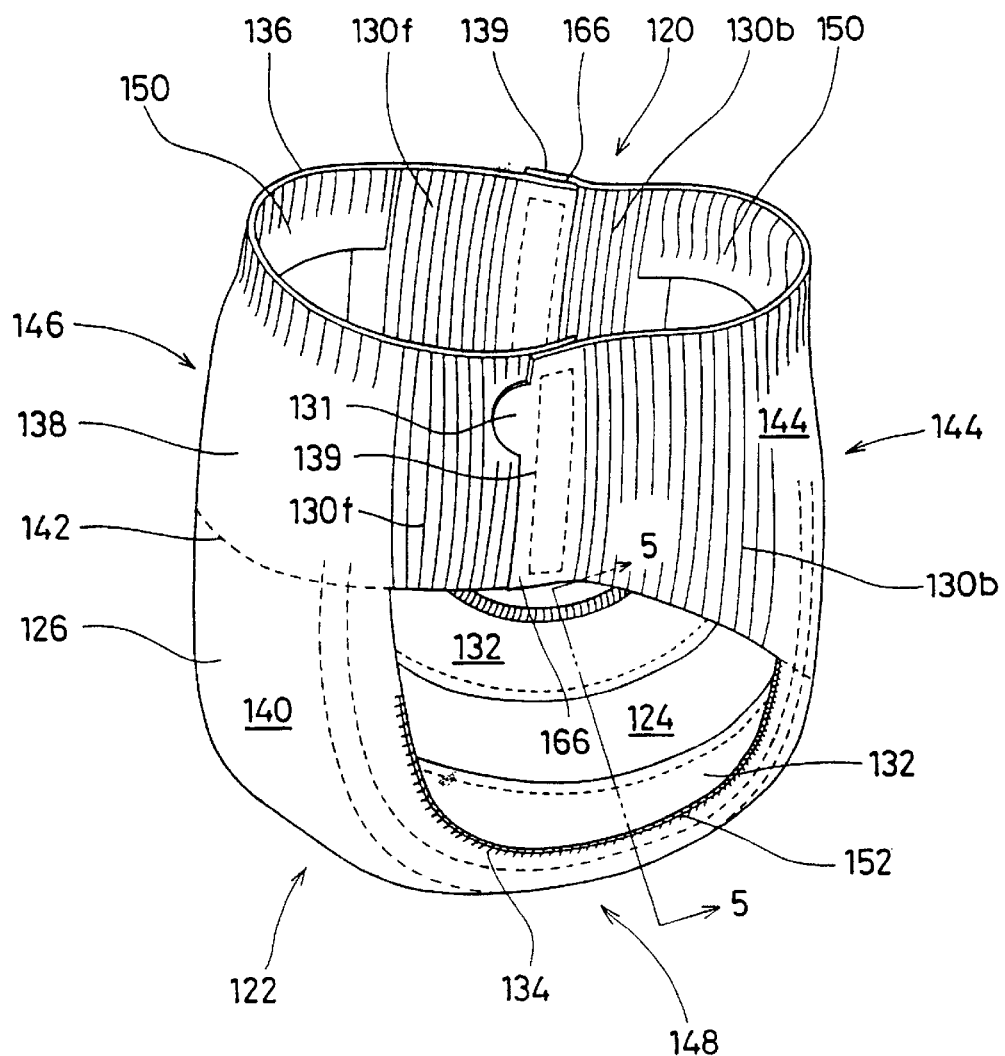
FIG. 4 is a perspective view of another preferred embodiment of the disposable absorbent article of the present invention in a typical in use configuration.

FIG. 4 is a perspective view of another preferred embodiment of the disposable absorbent article according to the present invention in a typical in use configuration. The disposable absorbent article of FIG. 4 shows a pull-on diaper 120. As used herein, the term "pull-on diaper" refers to diapers of wear which have a defined waist opening and a pair of leg openings and which are pulled onto the body of the wearer by inserting the legs into the leg openings and pulling the article up over the waist.

Referring to FIG. 4, the pull-on diaper 120 comprises a chassis 122 having a front waist region 146, a rear region 144 and a crotch region 148 between the front waist region 146 and the rear region 144. The chassis 122 comprises a liquid pervious topsheet 124, a liquid impervious backsheet 126 associated with the topsheet 124, and an absorbent core 128 (not shown in FIG. 4) disposed between the topsheet 124 and the backsheet 126. The pull-on diaper 120 further comprises front side panels 130f each extending laterally outwardly from the corresponding side of the chassis 122 in the front waist region 146; and back side panels 130b each extending laterally outwardly from the corresponding side of the chassis 122 in the rear region 144. As used herein, the term "panel" is used herein to denote an area or element of the pull-on garment. (While a panel is typically a distinct area or element, a panel may coincide (functionally correspond) somewhat with an adjacent panel.) The pull-on diaper 120 further comprises seam panels 166 each extending laterally outwardly from each of the front and back side panels 130f and 130b; and tear open tabs 131 each extending laterally outwardly from the seam panels 166. Additional preferred examples of the pull-on diaper 120 are disclosed in U.S. Pat. No. 5,569,234 to Buell et al. on Oct. 29, 1996.

The front and back side panels 130f and 130b can be any members which extend laterally outwardly from the corresponding side edges of the chassis 122. In preferred embodiments, each of the front and back side panels 130f and 130b is a projected member which projects laterally outwardly from the chassis 122. Preferably, the front side panels 130f and back side panels 130b are unitary elements of the pull-on diaper (i.e., they are not separately manipulative elements secured to the pull-on diaper, but rather are formed from and are extensions of one or more of the various layers of the pull-on diaper.) More preferably, each of the seam panels 166 is an extension of the corresponding front and back side panels 130f and 130b, or at least one of the component elements used therein, or any other combination of the elements. Preferably, each of the tear open tabs 131 is an extension of the corresponding seam panels 166 or at least one of their component elements used therein, or any other combination of the elements. In preferred embodiments, the front and side panels 130f and 130b are continuous members which continuously extend from the chassis 122. More preferably, at least one, preferably both of the front and back side panels 130f and 130b, comprises a continuous sheet or film material 142 which forms a part of the chassis 122 and continuously extends from the chassis 122. In alternative embodiments, the front and side panels 130f and 130b are discrete members (not shown in the figures) which are attached to the side edges of the chassis 122.

In a preferred embodiment, the front and back side panels 130f and 130b are elastically extensible in at least the lateral direction. As used herein, the term "elastically extensible" means a segment or portion that will elongate in at least one direction (preferably the lateral direction for the side panel) when tensional forces (typically lateral tensional forces for the side panel) are applied, and will return to about its previous size and configuration when the tensional forces are removed. More preferably, the front and back side panels 130f and 130b are elastically extensible both in the lateral and longitudinal directions.

The pull-on diaper 120 further comprises seams 139 each joining the corresponding seam panels 166 in an overlap manner to make an overlapped seam structure, thereby forming two leg openings 134 and a waist opening 136. The bonding of the seams 139 can be performed by any suitable means known in the art appropriate for the specific materials employed in the seam panels. Thus, sonic sealing, heat sealing, pressure bonding, adhesive or cohesive bonding, sewing, autogeneous bonding, and the like may be appropriate techniques. Preferably, the seam panels 166 are joined by a pattern of heat/pressure or ultrasonic welds.

A continuous belt 138 is formed about the waist opening 136. The continuous belt 138 acts to dynamically create fitment forces and to distribute the forces dynamically generated during wear. The pull-on diaper 120 thus preferably comprises a chassis layer 140; a first belt layer 142; and a second belt layer 144. Preferably, an elastic waist feature 150 is provided in both the front waist region 146 and the rear region 144. The pull-on diaper 120 additionally comprises elastic leg features 152. More preferably, apertures or vents (not shown) are provided in at least the side panels 130f and 130b of the pull-on diaper 120 to provide breathability and ventilation. Because the first belt layer 142 and the second belt layer 144 are preferably nonwoven webs having the appearance of cloth and the chassis layer 140 is preferably a plastic film, the pull-on diaper 120 has a unique aesthetic feature in that it is perceived by caregivers and wearers to have a garment-like comfort and feel in the waist regions while having a perceived containment benefit in the crotch region 148.

The continuous belt 138 is elastically extensible in the side panels 130f and 130b to provide a more comfortable and contouring fit by initially conformably fitting the pull-on diaper 120 to the wearer and sustaining this fit throughout the time of wear well past when it has been loaded with exudates by distributing forces along both the waist and legs since the sides of the pull-on diaper can expand and contract. The continuous belt 138 may be formed from a number of different materials and layers.

FIG. 5 is a cross-sectional view of the disposable pull-on diaper shown in FIG. 4 taken along the section line 5—5. The elasticized leg cuff 132 has a proximal edge 133 and a distal edge 135. The distal edge 135 of the elasticized leg cuff 132 is that part of the elasticized leg cuff 132 which is spaced away from the containment assembly 122 of the diaper when the diaper 120 is being worn. The proximal edge 133 is that part of the elasticized leg cuff 132 which is joined to the containment assembly 122 of the diaper 120. The proximal edge 133 is generally located laterally inboard of the periphery of the diaper 120. A portion of the elasticized leg cuff 132, however, may extend laterally outwardly from the proximal edge 133 such that the material covers at least a portion of the outer region of the backsheet. (not shown). An example of an elasticized cuff 132 having a portion extending laterally outwardly over most or all of the outer region of the backsheet 126 is described in the above-referenced U.S. Pat. No. 4,795,454 issued to Dragoo.

The elasticized barrier leg cuff 132 shown in FIG. 5 is formed by two single layer webs 93 and 94. One of the two single layer webs is a meltblown nonwoven web 93, the other is a spunbonded nonwoven web 94. The meltblown nonwoven web 93 and the spunbonded nonwoven web 94 are joined together to form the elasticized barrier leg cuff 132. The spunbonded nonwoven web 94 is folded at the distal edge 135 to enclose the spacing elastic members 195. The spunbonded nonwoven web 94 preferably extends to the side edge 150 of the diaper 120. Preferably, the meltblown nonwoven web 93 has a water resistance value of at least about 200 mmH$_2$O, and an average bending force value of less than about 20 mg cm$^2$/cm. More preferably, the meltblown nonwoven web 93 has a water resistance value of at least about 300 mmH$_2$O, and an average bending force value of less than about 15 mg cm$^2$/cm.

A preferred spunbonded nonwoven web 94 is a spunbond nonwoven of polypropylene obtainable from Fiberweb Co., Ltd., SC, USA as SOFSPAN (DAPP, 33 g/m$^2$). In an alternative preferred embodiment, the spunbonded nonwoven web 94 is a spunbonded nonwoven made of bi-component fibers. The bi-component fiber contains a polyethylene and a polypropylene. More preferably, the bi-component fiber has a core of the polypropylene and a sheath of the polyethylene. In preferred embodiments, the component fiber has from about 55% to about 95% by weight of the polyethylene. Most preferably, the bi-component fiber has from about 70% to about 90% by weight of the polyethylene.

III. EXAMPLES

Example I

10g/m$^2$ of a meltblown nonwoven web obtainable from Kuraray Co., Ltd., Osaka, Japan as PC0010EM is prepared. The nonwoven web is made of fine fibers of a polypropylene (PP). The fibers have the thickness of from about 3 $\mu$m to about 5 $\mu$m. This nonwoven web has a water resistance value of 300 mmH$_2$O, and a bending force value of 6 mg cm$^2$/cm. The embossment ratio (of the embossment roll) is 3.3%. The air permeability value is 47.0 cm$^3$/cm$^2$/sec. The maximum tensile strength value is 1.04 kfg. This nonwoven web is suitably used for the meltblown nonwoven web 93 of FIG. 5.

Example II

13g/m$^2$ of a meltblown nonwoven web obtainable from Kuraray Co., Ltd., Osaka, Japan as PC0013EM is prepared. The nonwoven web is made of fine fibers of a polypropylene (PP). The fibers have the thickness of from about 3 $\mu$m to about 5 $\mu$m. This nonwoven web has a water resistance value of 400 mmH$_2$O, and a bending force value of 13 mg cm$^2$/cm. The embossment ratio (of the embossment roll) is 3.3%. The air permeability value is 33.1 cm$^3$/cm$^2$/sec. The maximum tensile strength value is 1.39 kfg. This nonwoven web is also suitably used for the meltblown nonwoven web 93 of FIG. 5.

Example Ill

15g/m$^2$ of a meltblown nonwoven web obtainable from Kuraray Co., Ltd., Osaka, Japan as PCC0015EM is prepared. The nonwoven web is made of fine fibers of a polypropylene (PP). The fibers have the thickness of from about 3 $\mu$m to about 5 $\mu$m. This nonwoven web has a water resistance value of 500 mmH$_2$O, and a bending force value of 21 mg cm$^2$/cm. The embossment ratio (of the embossment roll) is 3.3%. The air permeability value is 24.5 cm$^3$/cm$^2$/sec. The maximum tensile strength value is 2.06 kfg. This nonwoven web is also suitably used for the meltblown nonwoven web 93 of FIG. 5.

Example IV 12 g/m$^2$ of a meltblown nonwoven web obtainable from Kuraray Co., Ltd., Osaka, Japan as KE7701 (Test Sample No.) is prepared. The nonwoven web is made of fine fibers of a polypropylene (PP). The fibers have the thickness of from about 7 μm to about 8 μm. This web is elongated along the machine direction by a tensile force after the production of the web. The elongation rate is about 70%. The basis weight of the original web is 17.5 g/m². The embossment ratio (of the embossment roll) of the original web is about 20%. This nonwoven web has a water resistance value of 190 mmH₂O, and a bending force value of 9 mg cm²/cm. The air permeability value is 116.7 cm³/cm²/sec. The maximum tensile strength value is 2.00 kfg. This nonwoven web is suitably used for the meltblown nonwoven web 92 of FIG. 3.

TABLE

|  | Example I | Example II | Example III | Example IV |
|---|---|---|---|---|
| Basis Weight (g/m²) | 10 | 13 | 15 | 12 |
| Water Resistance (mmH₂O) | 300 | 400 | 500 | 190 |
| Bending Force (mg cm²/cm) | 6 | 13 | 21 | 9 |
| Air Permeability (cm³/cm²/sec) | 47.0 | 33.1 | 24.5 | 116.7 |
| Maximum Tensile Strength (kgf) | 1.04 | 1.39 | 2.06 | 2.00 |
| Embossment Ratio (%) | 3.3 | 3.3 | 3.3 | 20 |

While particular embodiments of the present invention have been illustrated and described, it would be obvious to those skilled in the art that various other changes and modifications can be made without departing from the spirit and scope of the invention. It is understood that the examples and embodiments described herein are for illustrative purpose only and that various modifications or changes will be suggested to one skilled in the art without departing from the scope of the present invention.

What is claimed is:

1. A disposable absorbent article comprising:
   a liquid pervious topsheet;
   a liquid impervious backsheet combined with the topsheet;
   an absorbent core disposed between the topsheet and the backsheet; and
   a barrier cuff having a proximal edge and a distal edge, the proximal edge being joined to the topsheet and the distal edge being away from the top surface of the topsheet;
   wherein the barrier cuff comprises a single layer web having a water resistance value of at least about 150 mmH₂O, and an average bending force value of less than about 25 mg cm²/cm.

2. The disposable absorbent article of claim 1, wherein the single layer web has a basis weight of from about 3 g/m² to about 30 g/m².

3. The disposable absorbent article of claim 1, wherein the single layer web has an air permeability value of at least about 10 cm³/cm²/sec.

4. The disposable absorbent article of claim 1, wherein the single layer web has a maximum tensile strength value of at least about 0.7 kgf.

5. The disposable absorbent article of claim 1, wherein the single layer web is a meltblown nonwoven web.

6. The disposable absorbent article of claim 5, wherein the meltblown nonwoven web is made of fine fibers of a polyolefin.

7. The disposable absorbent article of claim 1, wherein the single layer web has an embossment pattern.

8. The disposable absorbent article of claim 7, wherein the embossment ratio of the single layer web is at least 0.5%.

9. The disposable absorbent article of claim 1, wherein the single layer web is elongated along its machine direction.

10. The disposable absorbent article of claim 9 wherein the elongation rate is from about 5% to about 150%.

11. The disposable absorbent article of claim 1, wherein the barrier cuff comprises a two layered structure of the single layer web having a water resistance value of at least about 150 mmH₂O, and a bending force value of less than about 21 mg cm²/cm.

12. The disposable absorbent article of claim 11, wherein the two layered structure is formed by folding at least a part of the single layer web.

13. The disposable absorbent article of claim 1 further comprising a spacing means combined with the barrier cuff for spacing the distal edge away from the top surface of the topsheet.

14. The disposable absorbent article of claim 13, wherein the spacing means has a spacing elastic member.

15. The disposable absorbent article of claim 13, wherein the barrier cuff is a barrier leg cuff or a barrier waist cuff.

* * * * *

UNITED STATES PATENT AND TRADEMARK OFFICE
CERTIFICATE OF CORRECTION

PATENT NO. : 6,420,627 B1
DATED : July 16, 2002
INVENTOR(S) : Ohnishi et al.

It is certified that error appears in the above-identified patent and that said Letters Patent is hereby corrected as shown below:

<u>Title page,</u>
Item [57], ABSTRACT,
Line 3, delete "previous" and insert -- pervious --.

<u>Column 1,</u>
Line 48, delete "Buff" and insert -- Butt --.
Line 64, delete "previous" and insert -- pervious --.

<u>Column 4,</u>
Line 13, delete "20" and insert -- 200 --.

<u>Column 5,</u>
Line 21, delete "wearers" and insert -- wearer's --.

<u>Column 6,</u>
Line 17, delete "previous" and insert -- pervious --.
Line 28, after an, delete ".".

<u>Column 7,</u>
Line 52, delete "eit" and insert -- et --.

<u>Column 11,</u>
Line 23, after "May 3, 1983;", delete ",".

<u>Column 13,</u>
Line 45, delete "it" and insert -- is --.

UNITED STATES PATENT AND TRADEMARK OFFICE
CERTIFICATE OF CORRECTION

PATENT NO. : 6,420,627 B1
DATED : July 16, 2002
INVENTOR(S) : Ohnishi et al.

It is certified that error appears in the above-identified patent and that said Letters Patent is hereby corrected as shown below:

<u>Column 16,</u>
Line 21, delete "component" and insert -- bi-component --.

Signed and Sealed this

First Day of June, 2004

JON W. DUDAS
*Acting Director of the United States Patent and Trademark Office*